(12) United States Patent
Grato

(10) Patent No.: US 6,177,579 B1
(45) Date of Patent: Jan. 23, 2001

(54) PROCESS FOR THE PREPARATION OF 13-CIS-RETINOIC ACID

(75) Inventor: Angelo Magnone Grato, Milan (IT)

(73) Assignee: Laboratori Mag S.p.A., Milan (IT)

( * ) Notice: Under 35 U.S.C. 154(b), the term of this patent shall be extended for 0 days.

(21) Appl. No.: 09/313,028

(22) Filed: May 17, 1999

(30) Foreign Application Priority Data

May 19, 1998 (IT) .............................................. MI98A1093

(51) Int. Cl.⁷ .................................................. C07C 51/353
(52) U.S. Cl. .............................................................. 554/125
(58) Field of Search ............................................... 881/125

(56) References Cited

FOREIGN PATENT DOCUMENTS

| | | |
|---|---|---|
| 3200231 | 7/1983 | (DE) . |
| 4313089 | 10/1994 | (DE) . |
| 0850925 | 7/1998 | (EP) . |

OTHER PUBLICATIONS

R.W. Curley Jr.: J. Org. Chem., vol. 49, No. 11, 1984 pp 1941–1944.
G. Pattenden Et Al: J. Chem Soc. (C), 1968 pp 1984–1997.

*Primary Examiner*—Deborah D. Carr
(74) *Attorney, Agent, or Firm*—Bucknam and Archer

(57) ABSTRACT

A process for the synthesis of 13-cis-retinoic acid with high purity and stability, without using heavy metals at any steps, starting from vinyl-beta-ionol prepared from ionone and vinyl magnesium halides.

6 Claims, No Drawings

PROCESS FOR THE PREPARATION OF 13-CIS-RETINOIC ACID

The present invention relates to a process for the preparation of 13-cis-retinoic acid. Said compound, of formula I

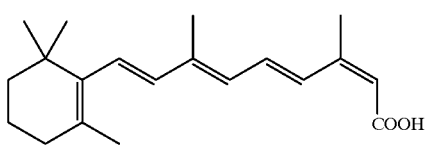

(I)

is a medicament (also known as "isotretinoin") with keratolytic activity, used particularly for the treatment of acne (see for further information, e.g. in "The Merck Index", 11$^{th}$ Ed., page 1299).

A number of processes for the preparation of compound I are known. Thus, G. Paddenten et al. (J. Chem. Soc. 1968, 1984–1997) disclose its synthesis starting from a [3-methyl-5(2,6,6-trimethyl-1-cyclohenen 1-yl-2,4-pentadienyl]-triphenyl-phosphonium) halide which is condensed according to Wittig with 5-hydroxy-1-methyl-2(5-H)-furanone (=4-hydroxy-3-methyl-butenolide). Said process yields, however, a mixture of the desired product with 11,13-di-cis-retinoic acid (11) and 11,13-di-trans-retinoic acid (III) isomers

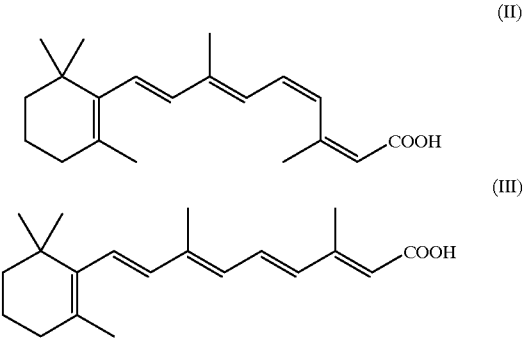

Therefore, compound (I), which is obtained in a markedly lower amount than (II) and in the smae amount as (III), has to be separated from the mixture by chromatography or fractional crystallization, with unsatisfactory yields.

EP 0 111 325 disclosed an improvement in the method by Paddenten, in which the Wittig condensation is carried out at tempertures ranging from −10 to −50° C., in alcoholic solvent and in the presence of alkali metal hydroxides, such as potassium hydroxide. A reaction product containing from 10 to 30% of the desired isomer (I) and from 70 to 90% of the isomer (II) is thereby obtained, with a conversion higher than 90% on the starting hydroxy-methyl-furanone. Said mixture, or the only isomer (II) separated therefrom, is subjected to isomerization in the presence of rhodium or palladium catalysts, to transform 11,13-di-cis-retinoic acid into the desired 13-cis-retinoic acid.

Said process, which provides 13-cis-retinoic acid in yields higher than those according to Paddenten, has however a drawback in that the isomerization of 11,13 di-cis-retionic acid involves the use of metals, such as rhodium and palladium, which are not only very expensive, but also difficult to separate from 13-ciis-retinoic acid. Furthermore, the presence of traces of said metal (or, more generally, of heavy metals) in 13-cis-retinoic acid, is not only in contrast with the required purity criteria, but also is a factor contributing to the known instability of the product (evidenced, inter alia, by X. Tan et al. in *Pharmaceutical Res.* 1992, (9), 1203–1208).

Palladium traces can also remain (and usually remain, unless a thorough purification is carried out, which is economically unacceptable) when operating according to the process claimed in DPR 1,059,900 and DPR 1,068,702 (and described by P. S. Manchard et al.,*J. Chem. Soc.,* 1965, 2019) for the synthesis of retinoids starting from vinyl-beta-ionol. Said intermediate has, in fact, been obtained from beta-ionone by reaction with acetylene (*J. Amer. Chem. Soc.,* 71, 2062 (1949) and subsequent reduction of the triplebond on a partially poisoned palladium catalyst.

Furthermore, DE 4,314,089 discloses a process for the preparation of 13-cis-retinoic acid in which the reaction between 4-hydroxy-3-methyl-butenolide and [3-methyl 5 (2,6,6-trimethyl-1-cyclohenen-1-yl)-2,4 pentadienyltri-arylphosphonium] salt is carried out in the presence of lithium hydroxide and dimethylformamide at temperatures ranging from 10 to 9° C., to give a mixture of 13-cis-retinoic and 11,13-di-cis-retinoic acids lithium salts, which are subsequently converted into the respective acids, by treatment with sulfuric acid. The resulting mixture is solubilised in alcoholic solvent and subjected to photochemical isomerization to obtain 13-cis-retinoic acid.

This process is a remarkable improvement compared with the prior art, in that the isomerization requires no use of said catalysts, but it also has a series of drawbacks, as the photochemical isomerization is carried out on the mixture of retinoic acids which are per se poorly soluble in the reaction solvents compatible with said photochemical isomerization: as a matter of fact, solutions containing the above mentioned mixture of acids in concentrations below 10% have to be used.

On an industrial scale, the process therefore requires remarkable amounts of solvents, to the detriment of the economy of the process as well as the safety of the workers.

Furthermore, such mixture of acids is rather unstable in said organix solvents, also due to traces of palladium from vinyl-beta-ionol (IV).

Said drawbacks have partially been overcome by the Italian Patent application MI 94 A 002752 in the Applicant's name, in which photoisomerization is carried out on the aqueous solution of a 11,13-di-cis-retinoic acid alkali salt. However, this process also involves the drawback due to the presence of palladium traces.

It has now been found a novel process which provides 13-cis-retionoic acid in a highly stable and pure state, thanks to a synthetic pathway which avoids at any step the use of palladium or other heavy metals. Said synthesis combines the advantages of photochemical isomerization on the 11,13-di-cis-retinoic acid alkali salt (or on alkali salts of the mixture of acids from the preceding Wittig condensation) by use of vinyl-beta-ionol (IV) obtained according to the invention—from beta-ionone and a vinyl magnesium halide.

The process according to the invention can be summarized as follows.

A) beta-ionone (IV) is reacted with a vinyl magnesium halide (V) (chloride, iodide or—preferably—bromide):

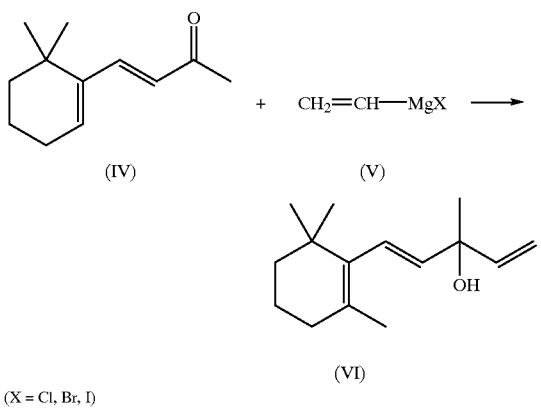

(X = Cl, Br, I)

B) resulting vinyl-beta-ionol (VI) is subjected to Wittig condensation with 4-hydroxy-3-methyl butenolide (VII) according to the process by Paddenten (see above) or to that disclosed in EP 115,325, the reaction product consisting of a mixture of 13-cis-retinoic acid (I), 11,13-di-cis-retinoic acid (II) and 11,13-di-trans-retinoic acid (III):

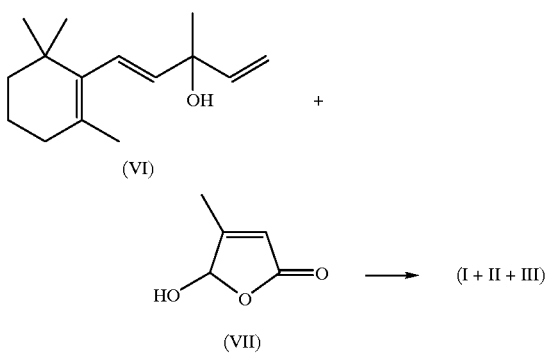

C) the alkali metal salts of the resulting mixture of the three acids, dissolved in water, are subjected to photochemical isomerization in aqueous solution, to give 13-cis-retinoic acid (I) with high purity and stability.

Step A) of the process of the invention is carried out under Grignard reaction conditions (well known to those skilled in the art), at tempertures ranging from −40° C. to +50° C., preferably from −15° C. to −30° C. A preferred solvent is tetrahydrofuran, but other ethers may also be used. The vinyl magnesium halide used is preferably the bromide. At the end of the reaction, product (VI) is recovered with conventional techniques.

Step B), as already mentioned, can be carried out following the conventional procedure by Paddenten or the modified disclosed in EP 115,325.

The operative details of step C) are those claimed in the already cited Italian Patent application (MI96A-002752) in the Applicant's name, with the advantages—compared with the prior art—disclosed in said application, and can be summarized as follows: higher stability of (I) alkali salts in aqueous solution compared with thee free acid in organic solvents; higher reaction rate; higher economy and, above all, lower risks on an industrial scale; operative advantages deriving from the use of solution of nearly triple concentration compared with those used with organic solvents.

The following examples further illustrate the process according to the invention.

EXAMPLE 1

Vinyl beta-ionol 1.3 mols of magnesium turnings are placed in a 3 L four-necked flask. 100 ml of tetrahydrofuran (THF) and a iodine crystal are added thereto. 50 ml of a 15% vinyl bromide solution in tetrahydrofuran are added with stirring and under nitrogen atmosphere. The solution immediately decolourizes, while the Grignard starts to form with an exothermic reaction: the mixture is cooled to −30° C. and one mol of beta-ionone dissolved in 500 ml of THF and 950 mL of the above 15% vinyl bromide solution are added at the same time through two dropping tunnels, at such a rate that temperature remains below −15 20° C. After completion of the addition, the cooling bath is removed and the reaction mixture is brought to room temperature. After 2 hours the reaction mixture is poured into 2 ml of ice-water containing 10 g of ammonium chloride under stirring, then is extracted with 700 ml of ethyl acetate. The organic phase is washed twice with 100 ml of 15% sodium chloride aqueous solution and dried over sodium sulfate. Solvent is evaporated off under reduced pressure and the resulting thick oil is distilled under vacuum, collecting 202 g of distillate, consisting of vinyl beta-ionol of purity higher than 95%, as determined by NMR analysis (yield: 87.5%).

EXAMPLE 2

Vinyl beta-ionol

A solution of 6.9 kg of vinyl bromide in 42 kg of tetrahydrofuran is added under nitrogen, with stirring to 1.45 kg of magnesium turnings in the presence of 4 kg of tetrahydrofuran, at such a rate that inner temperature does not exceed 50° C. After completion of the addition the reaction mixture is stirred for 1 hour.

This mixture is added with 8.75 kg of beta-ionone at such a rate that temperature does not exceed 30° C., and it is left at this temperature for 8 hours with stirring; subsequently the reaction mixture is poured, into a cold mixture of 3.6 kg of ammonium chloride and 2.5 kg of acetic acid in 48 kg of water, with stirring.

16.5 kg of ethyl acetate are added and the organic phase is separated after prolonged stirring. The organic phase is separated and repeatedly washed with water, then evaporated under vacuum to obtain 9.4 kg of a residue containing not less than 7.5 kg of vinyl beta-ionol (by gaschromatographic and NMR analysis) (yield: 75%).

EXAMPLE 3

Vinyl beta-ionol 0.1 mols of magnesium turnings are suspended in 50 ml of THF and treated with some drops of a solution of 0.12 mols of vinyl bromide in 100 ml of THF with stirring and under nitrogen atmosphere. As soon as the Grignard starts to form, the mixture is is cooled to 5–10° C. and added with the remaining solution of vinyl bromide in 30 min. The mixture is then cooled to −60° C. and added with 0.09 mols of beta ionone in 100 ml of THF in 20 min. The mixture is left to warm to room temperature, then heated at 40° C. for 2 hours. After that, the reaction is quenched as above described and vinyl beta-ionol is recovered by double distillation under vacuum, to obtain 166 g of a product, corresponding to an about 84% yield, with purity higher than 90%, determined by NMR.

EXAMPLE 4
Mixture of retinoic acids from vinyl beta-ionol and 4-methyl-3-hydroxy-butenolide 7.5 kg of vinyl beta-ionol, with a 98% NMR purity, in 35 kg of ethanol are added with 9 kg of triphenylphosphine then with gas hydrochloric acid until pH of the solution remains acid. The solution is cooled to 40° C. and added simultaneously at this temperature with 7 kg of hydroxy butenolide and 9 kg of potassium hydroxide in 27 kg of ethanol, using two separate funnels. After completion of the addition, the reaction mixture is kept at −40° C. for a further two hours, then added with 34 kg of hexane and 150 kg of water. The hexane phase is separated and the aqueous phase is washed again with further 20 kg of hexane. The cold basic aqueous phase is treated with concentrated hydrochloric acid under stirring, in the presence of a 6:4 hexane-ethyl acetate mixture (30 kg), to markedly acid pH. The procedure is repeated with 10 kg more of the mixture. The organic phase containing the desired mixture of retinoic acids is evaporated to dryness.

The typical composition of this crude is:

| | |
|---|---|
| 13-cis-retinoic acid | 25–35% |
| 11,13-di-cis-retinoic acid | 50–65% |
| 11,13-di-trans-retinoic acid | 5–10% |
| others | 5–10% |

EXAMPLE 5
13-cis-Retinoic acid

The mixture obtained above is dissolved in a solution of 1.6 kg of potassium hydroxide in 12 kg of water. The aqueous solution is added with 2 g of Bengal rose and the mixture is placed in a glass container to be subjected to the action of metal halide lamps of 1800 Watt total potency. The isomerization reaction requires on the average 8 hour irradiation. The progress of reaction is checked by HPLC analysis, controlling that the final content in 11,13-di-cis-retinoic acid does not exceed 1%. The reaction mixture is then cooled and treated under stirring with cold 25% sulfuric acid to acid pH. The mixture is then extracted with 19 kg of cyclohexane in the hot. The cyclohexane solution is cooled to obtain a crude which is recrystallized to give 3 kg of 13-cis-retinoic acid, containing less than 0.5% impurities. The crystallization solvents can be cyclohexane itself or toluene, or alcohols such as ethanol, isopropanol, or higher alcohols, or esters such as methyl, ethyl or isopropyl acetates. The solvent mixtures reported above are also useful.

EXAMPLE 6
13-cis-Retinoic acid 43 g of the mixture of retinoic acids from the condensation of hydroxy butenolide, vinyl beta-ionol and triphenylphosphine hydrochloride in 10 ml of ethanol are treated with 15 g of a 50% potassium hydroxide aqueous solution, subsequently diluted to 200 mL with water, added with 30 mg of Bengal rose, then irradiated with a 18 Watt lamp for 12 hours.

The final composition of the mixture is typically the following:

| | |
|---|---|
| 13-cis-retinoic acid | 1% |
| 11,13-di-trans-retinoic acid | 22.5% |
| 11,13-di-cis-retinoic acid | 0.2% |

The reaction mixture is acidified with sulfuric acid, as in the above example, extracted with hot cyclohexane and subsequently cooled to give a crystalline crude weighing 19 g.

The composition of this product is typically the following:

| | |
|---|---|
| 13-cis-retinoic acid | 97.8% |
| 11,13-di-trans-retinoic acid | 2% |
| 11,13-di-cis-retinoic acid | 0.2% |

The resulting product is subsequently crystallized from ethanol or ethyl acetate to yield 13-cis-retinoic acid with purity higher than 99.5%.

What is claimed is:
1. A process for the preparation of 13-cis-retinoic acid (I)

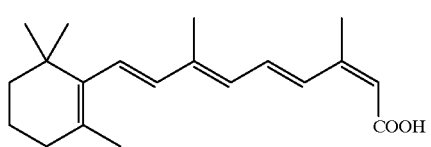

(I)

free from heavy metals traces, comprising the following steps:

a) reacting beta-ionone (IV) with a vinyl magnesium halide (V):

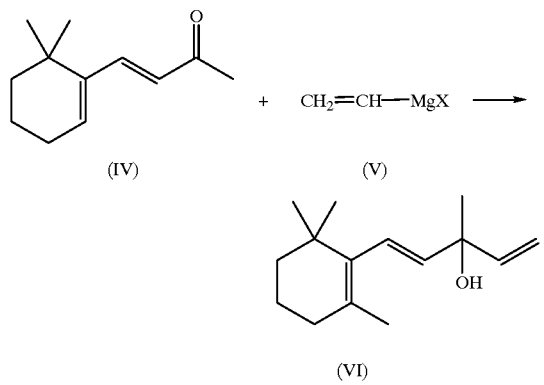

(X—Cl, Br, I)

to give vinyl-beta-ionol (VI);

b) carrying out a Wittig condensation of vinyl-beta-ionol (VI) with 4-hydroxy-3-methyl-butenolide (VII) according to conventional methods to give a mixture of 13-cis-retinoic acid (I), 11-13-di-cis-retinoic acid (II) and 11,13 di-trans-retinoic acid (III):

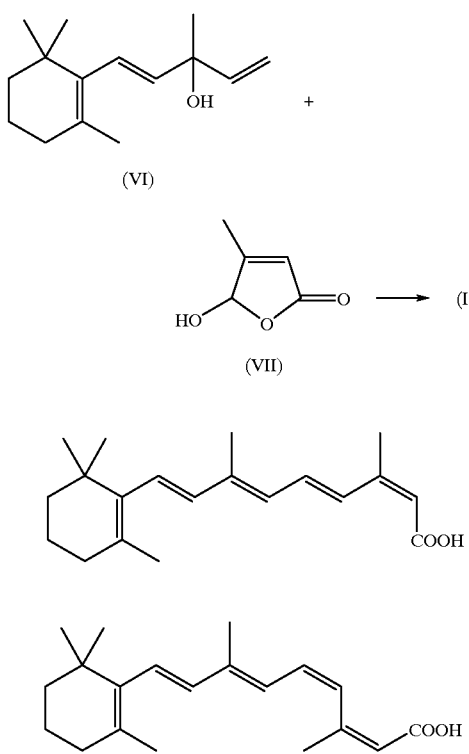

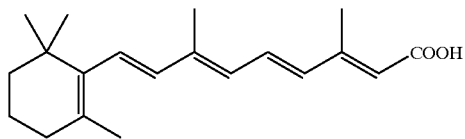

c) carrying out a photochemical isomerization, in an aqueous solution, of the alkali metal salts of the acids from step b).

2. The process as claimed in claim 1, wherein step a) is carried out with vinyl magnesium bromide.

3. The process according to claim 1, wherein step a) is carried out at temperatures ranging from −40° C. to +50° C.

4. The process as claim in claim 1, which is carried out at temperatures ranging from −15° C. to −30° C.

5. The process according to claim 1, wherein step a) is carried out in tetrahydrofuran.

6. 13-cis-retinoic acid free from heavy metals traces.

* * * * *